United States Patent [19]

Kanno et al.

[11] Patent Number: 4,758,325

[45] Date of Patent: Jul. 19, 1988

[54] ION SELECTIVE ELECTRODE AND FLOW TYPE ION SENSOR USING THE SAME

[75] Inventors: Ken-ichi Kanno; Tetsuya Gatayama; Masao Koyama, all of Yokohama, Japan

[73] Assignee: Kabushiki Kaisha Toshiba, Japan

[21] Appl. No.: 817,798

[22] Filed: Jan. 10, 1986

Related U.S. Application Data

[63] Continuation of Ser. No. 610,009, May 14, 1984, abandoned.

[30] Foreign Application Priority Data

May 19, 1983 [JP] Japan .................. 58-86630

[51] Int. Cl.[4] ............................................. G01N 27/46
[52] U.S. Cl. ...................................... 204/411; 204/412; 204/416; 204/418
[58] Field of Search ............... 204/409, 411, 412, 415, 204/416, 418, 435; 128/635

[56] References Cited

U.S. PATENT DOCUMENTS

| | | | |
|---|---|---|---|
| 3,556,950 | 1/1971 | Dahms | 204/411 |
| 3,718,568 | 2/1973 | Neuwelt | 204/412 X |
| 3,835,013 | 9/1974 | Grubb et al. | 204/415 |
| 3,856,636 | 12/1974 | Grubb | 204/415 |
| 3,997,420 | 12/1976 | Buzza | 204/412 X |
| 4,020,830 | 5/1977 | Johnson et al. | 204/418 X |
| 4,233,031 | 11/1980 | Matson et al. | 204/412 X |
| 4,349,426 | 9/1982 | Sugahara et al. | 204/418 |
| 4,388,165 | 6/1983 | Koshiishi et al. | 204/418 |
| 4,404,065 | 9/1983 | Matson | 204/411 X |
| 4,409,088 | 10/1983 | Kanno et al. | 204/418 X |
| 4,452,682 | 6/1984 | Takata et al. | 204/416 X |
| 4,533,457 | 8/1985 | Watanabe | 204/411 |

FOREIGN PATENT DOCUMENTS 3010461 10/1981 Fed. Rep. of Germany ...... 204/411
55-154454 7/1980 Japan .

OTHER PUBLICATIONS

"Transport Phenomena in Membranes", Academic Press (1969), N. Lakshminarayanaiah, pp. 292-297.

Primary Examiner—John F. Niebling
Assistant Examiner—Nam X. Nguyen
Attorney, Agent, or Firm—Foley & Lardner, Schwartz, Jeffery, Schwaab, Mack, Blumenthal & Evans

[57] ABSTRACT

There are disclosed an ion selective electrode comprising a polyvinyl chloride series resin plate having a through hole; conductive member disposed along the through hole; ion sensitive membrane of a polyvinyl chloride series resin membrane; and a lead wire connected to the conductive member, and the flow type ion sensor comprises a plurality of the ion selective electrodes mutually integrally associated with each other with the interposition of electrical insulating members so that through holes of the respective ion selective electrodes may define a flow passage for a liquid to be measured, and a flow type ion sensor using the same.

The ion selective electrode and flow type ion sensor using the same of this invention allow the measurement in a smaller amount of the sample to be measured and are excellect in the adhesion of the ion sensitive membranes, therefore they have effects of a stable potential supply and a prolonged life time, and these industrial merits are highly great.

13 Claims, 1 Drawing Sheet

ION SELECTIVE ELECTRODE AND FLOW TYPE ION SENSOR USING THE SAME

This application is a continuation of application Ser. No. 610,009, filed May 14, 1984, now abandoned.

BACKGROUND OF THE INVENTION

This invention relates to an ion selective electrode and a flow type ion sensor using the same, capable of selectively measuring specific ion concentrations.

More specifically, it relates to an ion selective electrode and a flow type ion sensor using the same which are excellent in the adhesion of an ion sensitive membrane, and thus indicate stable potentials, and have a prolonged life time.

The ion selective electrode can characteristically accomplish a selectivity quantitative determination of specific ion concentrations in a liquid, and it has heretofore been used in many fields such as monitoring of specific ion concentrations and water analysis.

For example, in the case that an ion selective electrode to be used is a cation selective electrode, a relation between an activity $a+$ of an aimed cation and a potential E indicated by the cation selective electrode is represented as follows:

$$E = E^0 + 2.303(RT/zF)\log a+ \quad (1)$$

Further, in the case of an anion selective electrode, a relation between an activity $a-$ of an aimed anion and a potential E indicated by the anion selective electrode is represented as follows:

$$E = E^0 + 2.303(RT/zF)\log a- \quad (2)$$

As understood from them, a logarithm of the activity and the potential are in a proportional relation, therefore the activity of the aimed ion can easily be obtained from a measured potential value.

In the aforementioned formulae (1) and (2), R is gas constant, T is absolute temperature, z is an ion value, F is Faraday constant and $E^0$ is a standard electrode potential in a system.

If the ion selective electrodes mentioned above are used, a measurement of the potentials will easily permit the quantitative determination of the ion concentrations in an extensive range. Further, if the ion selective electrodes having the small-size electrode members are employed, the determination will be possible even for a small amount of a sample. As is definite, such ion selective electrodes are convenient, therefore they are often utilized of late in a medical field, particularly for the measurement of various ions such as $Na^{30}$, $K^{30}$ and $Cl^-$ present in a blood.

Moreover, a variety of analytical instruments each in which the aforementioned ion selective electrodes are used has actually been devised, and their uses are now getting expensive as analytical instruments for bloods and the like in the medical field.

Of these ion selective electrodes, ones having simple structure are popular particularly because of easiness of its manufacture, handling and maintenance, in which simple structure each ion sensitive membrane is formed directly on a metal member without any internal electrolyte solution.

Additionally, as a method of successively measuring the respective concentrations of plural kinds of ions in the liquid to be measured, a so-called flow cell system is known in which a plurality of ion selective electrodes is disposed in parallel across a flow passage of the liquid sample, and electrical signals from the respective electrodes are then analyzed.

Moreover, in recent years, there has been developed a flow type ion sensor in which ion selective electrodes without any internal electrolyte solution are integrally coupled in a flow cell system.

In this flow type ion sensor, the passage for the liquid to be measured is defined by electrode surfaces of a plurality of ion selective electrodes, therefore it is feasible to render its structure small-size and multifunctional, further, advantageously a less amount of the liquid to be measured suffices to accomplish the ion analysis.

In such a flow type ion sensor, each pipe of a noble metal such as gold or silver is coated with an ion sensitive membrane.

However, the flow type ion sensor comprising such noble metal pipes is costly, as a great amount of the noble metal material is used, and the adhesion between the metal and the ion sensitive membrane is bad, thereby disadvantageously shortening its life time.

For this reason, another electrode has been suggested in which a plastic plate is provided with a through hole for allowing a liquid sample to flow therethrough, and a metallic thin membrane is mounted on a part of the inner surface of the through hole, instead of the metal pipe.

With regard to this flow type ion sensor including the plastic plate, it can be inexpensive because of a less metallic material, and not only the metallic surface but also the plastic surface adjacent to the above metallic surface portion is extensively coated with the ion sensitive membrane, whereby the improvement in the adhesion of the ion sensitive membrane can be expected.

Materials for the plastic plate which have heretofore been used for such a purpose include an acrylic resin, a phenolic resin, an epoxy resin and the like.

However, the adhesion between the plastic plate and the polyvinyl chloride resin membrane of an ion sensitive membrane material is not as good as expected. As a result, peeling of the membrane often will occur, so that the liquid to be measured will be contiguous to the metallic plate to bring about a short, and obtained potentials will thus be unstable and the life time of the ion sensor will be noticeably shortened.

An object of the invention is to provide an ion selective electrode and a flow type ion sensor using the same which are excellent in an adhesion of an ion sensitive membrane, and can thus give stable potentials, and a prolonged life time.

SUMMARY OF THE INVENTION

The inventors of the present case have conducted intensive research with the intention of achieving the aforesaid object, and as a result, it has been found that in the ion selective electrode in which through holes provided in plastic plates are employed as a flow passage for a liquid to be measured, if polyvinyl chloride resin plates are utilized as the plastic plates and ion sensitive membranes comprising polyvinyl chloride series resin membranes are applied to the inner surfaces of the through holes, an adhesion of the ion sensitive membrane is noticeably improved, and in consequence, the present invention has now been accomplished.

That is to say, according to this invention, there is provided an ion selective electrode which comprises a polyvinyl chloride series resin plate having a through hole;

conductive member disposed along said through hole provided in the polyvinyl chloride series resin plate so as to form at least a part of an inner peripheral surface of said through hole;

ion sensitive membrane of a polyvinyl chloride series resin with which said conductive member forming the inner peripheral surface of said through hole is covered on the whole surface thereof and with which said polyvinyl chloride series resin plate adjacent to the surface of said conductive member is covered on at least a part of the inner peripheral surface thereof; and a lead wire connected to said conductive member.

Further, a flow type ion sensor according to this invention comprises a plurality of ion selective electrodes mutually integrally associated with each other with the interposition of electrical insulating members so that through holes of said respective ion selective electrodes may define a flow passage for a liquid to be measured, the ion selective electrodes each being composed of:

a polyvinyl chloride series resin plate having a through hole;

conductive member disposed along said through hole provided in the polyvinyl chloride series resin plate so as to form at least a part of an inner peripheral surface of said through hole;

ion sensitive membrane of a polyvinyl chloride series resin with which said conductive member forming the inner peripheral surface of said through hole is covered on the whole surface thereof and with which said polyvinyl chloride series resin plate adjacent to the surface of said conductive member is covered on at least a part of the inner peripheral surface thereof; and a lead wire connected to said conductive member.

DESCRIPTION OF THE PREFERRED EMBODIMENTS

Figure 1:
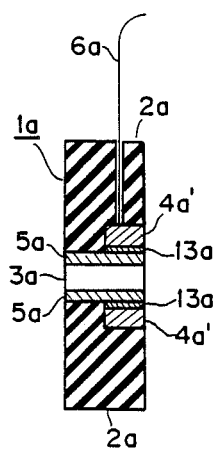
FIG. 1 is a conceptional section of one embodiment of a sodium ion selective electrode regarding this invention.

The polyvinyl chloride series resin plate used in the ion selective electrode according to this invention is an essential constitutional element for supporting the conductive member and for serving to improve the adhesion of the polyvinyl chloride series resin membrane of the ion sensitive membrane material.

The polyvinyl chloride series resin plate may comprise a polyvinyl chloride homopolymer or a copolymer of vinyl acetate, vinylidene chloride, acrylonitrile or the like, and it may contain a well-known plasticizer, stabilizer, filler and the like.

Further, the polyvinyl chloride series resin plate may take any configuration such as a disc, square or rectangle.

The thickness of the plate is preferably 1 mm or more, more preferably within 2 to 10 mm. If the plate thickness is less than 1 mm, an area of the electrode will be small and an obtained potential will be difficult to stabilize; on the other hand, if it is more than 10 mm, the flow passage for the liquid to be measured will become too long, which fact require a great deal of the liquid to be measured for the ion analysis.

The through hole provided in each polyvinyl chloride series resin plate may take any configuration such as a cylinder, square pillar or prism. In the instance where the through hole is cylindrical, it usually has a diameter of 1 to 3 mm. This reason is that if its diameter is less than 1 mm, a stream of the liquid to be measured will be bad and the potential will thus be unstable, and if it is more than 3 mm, a great deal of the liquid sample will be required for the accomplishment of the ion analysis.

The conductive member above is an element for supporting the ion sensitive membrane and for collecting electrical signals.

Materials for the conductive member include well-known electrode materials, for example, metals such as gold, silver, copper and platinum as well as alloys thereof and graphite. Among these, silver is particularly preferable, and it is more preferred that a thin layer of a metallic compound such as an oxide or halide is formed on the metal surface. If the thin layer of the metallic compound is present on the metal surface, the adhesion of the ion sensitive membrane will be improved, and a potential fluctuation resulting from a corrosion on the metal surface and the like will be additionally prevented.

This conductive member is connected with a lead wire for transmitting the electrical signals in the ion sensitive membrane to a measuring system.

A material of the ion sensitive membrane regarding this invention should be a polyvinyl chloride series resin.

This polyvinyl chloride series resin of the membrane material may be the same as or different from the resin constituting the aforesaid polyvinyl chloride series resin plate.

The ion sensitive membrane used in this invention contains, in the polyvinyl chloride series resin membrane, at least an ion selective substance such as monensin, valinomycin, a quaternary ammonium salt or a crown ether and a plasticizer such as dioctyl adipate, dioctyl phthalate and orthonitrophenyl octyl ether.

In the flow type ion sensor according to this invention, the ion selective electrodes are linked in series with each other so that opening edges of the adjacent through holes may be fitted to each other.

Examples of the electrical insulating members includes rubbers and plastics.

It is preferable that an electrical resistance of these insulating members is not less than that of the ion sensitive membrane.

In this invention, it is preferred that a reference electrode is further provided and is mutually integrally associated with the aforesaid plurality of ion selective electrodes with the interposition of electrical insulating members so that the through holes thereof may define the flow passage for the liquid to be measured.

In the reference electrode used in this invention, it is preferable that the reference electrode comprises a polyvinyl chloride series resin plate having a through hole; conductive member disposed along said through hole provided in the polyvinyl chloride series resin plate so as to form at least a part of an inner peripheral surface of said through hole; polyvinyl chloride series resin membrane with which said conductive member forming the inner peripheral surface of said through hole is coated on the whole surface thereof and with which said polyvinyl chloride series resin plate adjacent to the surface of said conductive member is coated on at least a part of the inner peripheral surface thereof; silicone series polymer membrane with which said polyvinyl chloride series resin membrane is coated on the surface thereof; and a lead wire connected to said conductive member.

Among these, the reference electrode comprising a silver-silver halide electrode which requires no internal electrolyte solution and indicates a stable standard potential is preferable, and it is particularly preferable that a silver-silver halide electrode comprises a conductive member of a silver member; a silver halide layer formed on at least a part of the surface of the silver member, preferably on whole surface of the silver member in view of the adhesion; a polyvinyl chloride series resin membrane layer with which the silver halide layer is formed on the surface thereof and which contains potassium chloride; and a silicone polymer membrane with which the polyvinyl chloride series resin membrane layer is coated on the surface thereof. Further, in this case, it is preferable that the plastic plate having the through hole comprises the polyvinyl chloride series resin plate.

If the reference electrode is embedded in the ion sensor according to this invention, an ion concentration measuring apparatus will further be miniaturized and the measurement will be carried out in a smaller amount of the liquid to be measured.

Moreover, the ion sensor according to this invention is preferably surrounded with an outer case having an inlet and an outlet for the liquid to be measured which communicate with the through holes and having an electrical signal output opening for leading out the lead wires.

The disposition of such an outer case permits a noticeably easy handling of the ion sensor according to this invention.

Now, the ion selective electrode and the ion sensor according to this invention will be described in reference to the accompanying drawings.

FIG. 1 is a conceptional section of one embodiment of an ion selective electrode regarding this invention.

In this drawing, a polyvinyl chloride resin plate 2a is provided at the central portion thereof with a through hole 3a, and a silver member 4a' mounted along the through hole 3a forms a part of an inner peripheral surface of the through hole 3a. This silver member 4a' is covered on the surface thereof with a silver chloride layer 13a. The inner peripheral surface of the through hole 3a comprising the silver member 4a' and the polyvinyl chloride resin plate 2a is coated with an ion sensitive membrane 5a comprising the polyvinyl chloride series resin, ion selective substance and plasticizer, and this ion sensitive membrane 5a forms an ion concentration-measuring surface for the liquid sample which runs through the through hole 3a.

Figure 2:
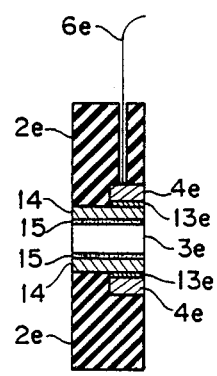
FIG. 2 is a conceptional section of a reference electrode used in one preferred embodiment according to this invention.

FIG. 2 is a conceptional section of a reference electrode used in one preferred embodiment according to this invention.

In this drawing, the polyvinyl chloride resin plate 2e is provided at the central portion thereof with the through hole 3e, and the silver member 4e, mounted along the through hole 3e forms a part of the inner peripheral surface of the through hole. This silver member 4e is covered on the surface thereof with a silver chloride layer 13e. An inner peripheral surface of the through hole 3e comprising the silver member 4e and the polyvinyl chloride resin plate 2e is coated with the polyvinyl chloride series resin membrane 14 containing potassium chloride, and this polyvinyl chloride series resin membrane is protected by a protective membrane 15 of a silicone polymer.

Figure 3:
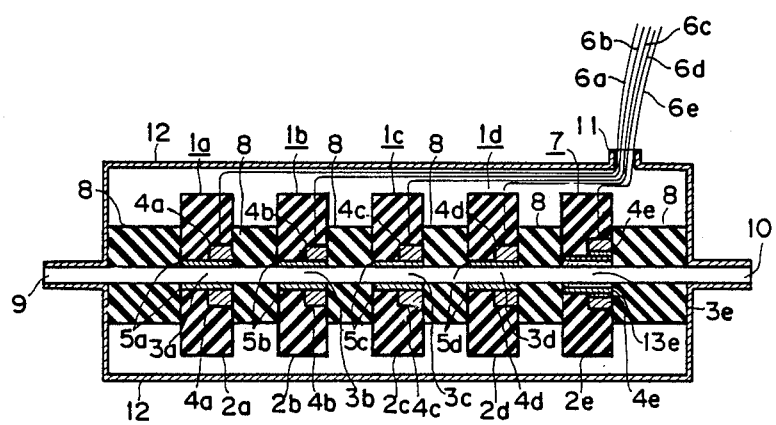
FIG. 3 is a conceptional section illustrating one embodiment of the ion sensor according to this invention.

FIG. 3 is a conceptional section illustrating one embodiment of the ion sensor according to this invention.

In this drawing, reference numerals 1a, 1b, 1c and 1d represent a sodium, a potassium, a calcium and a chloride ion selective electrode, respectively. These ion selective electrodes 1a, 1b, 1c and 1d comprise polyvinyl chloride resin plates 2a, 2b, 2c and 2d, respectively, these resin plates being provided in the central portions thereof with the through holes 3a, 3b, 3c and 3d, respectively. Further, the conductive members 4a, 4b, 4c and 4d each mounted along the through holes 3a, 3b, 3c and 3d forms a part of each inner peripheral surface of the holes. The through holes 3a, 3b, 3c and 3d are coated on the inner peripheral surfaces thereof with ion sensitive membranes 5a, 5b, 5c and 5d, respectively, comprising the polyvinyl chloride series resin membranes, and these ion sensitive membranes 5a, 5b, 5c and 5d are selectively sensitive to ions in the liquid to be measured which is running through the through holes 3a, 3b, 3c and 3d, in order to generate an electromotive force corresponding to each ion concentration. Electrical signals generated in the ion sensitive membranes 5a, 5b, 5c and 5d are led to a potential indicating device (not shown) via the conductive members 4a, 4b, 4c and 4d as well as the lead wires 6a, 6b, 6c and 6d, respectively.

Further, reference numeral 7 represents a reference electrode disposed on the inner peripheral surfaces of the through holes 3a, 3b, 3c and 3d which are provided in the plastic plates. An electric signal in the reference electrode is led to the potential indicating device (not shown) via a lead wire 6e, and in the potential indicating device, difference between the standard potential from the reference electrode 7 and the potentials from the ion selective electrodes 1a, 1b, 1c and 1d are displayed.

These ion selective electrodes 1a, 1b, 1c and 1d as well as the reference electrode 7 are mutually integrally associated with each other with the interposition of an electrical insulating member 8 so that the through holes 3a, 3b, 3c and 3d may define the flow passage for the liquid to be measured.

Further, this flow type ion sensor is surrounded with an outer case 12 having an inlet 9 and an outlet 10 for the liquid to be measured which communicate with the through holes 3a, 3b, 3c, 3d and 3e, and having an electrical signal output opening 11 for leading out the wires 6a, 6b, 6c, 6d and 6e.

In order to form the coating layers of the ion sensitive members 5a, 5b, 5c and 5d on the inner peripheral surfaces of the through holes 3a, 3b, 3c and 3d which are provided in the polyvinyl chloride series resin plates 2a, 2b, 2c and 2d, for example, the following procedure may be employed.

In the first place, the polyvinyl chloride series resin, an ion selective material such as monensin, valinomycin, a quaternary ammonium salt or a crown ether and a plasticizer such as dioctyl adipate, dioctyl phthalate or orthonitrophenyl octyl ether are dissolved in a solvent such as tetrahydrofuran to obtain an ion sensitive membrane-forming solution.

In the next place, the thus obtained solution is applied to the inner peripheral surfaces of the through holes 3a, 3b, 3c and 3d in the polyvinyl chloride series resin plates 2a, 2b, 2c and 2d, followed by drying, in order to form the desired ion sensitive membrane layers 5a, 5b, 5c and 5d thereon.

In this invention, the polyvinyl chloride series resin plates 2a, 2b, 2c and 2d are coated with the ion sensitive membranes 5a, 5b, 5c and 5d comprising the polyvinyl chloride series resin, therefore the adhesion therebetween is extremely good. In particular, when the ion sensitive membrane-forming solution which contains the solvent of tetrahydrofuran or the like is applied to the polyvinyl chloride series resin plates 2a, 2b, 2c and 2d in order to form the ion sensitive membranes 5a, 5b, 5c and 5d, the adhesion of the ion sensitive membranes 5a, 5b, 5c and 5d to the plate can be further enhanced, as surface layers on the polyvinyl chloride series resin plates 2a, 2b, 2c and 2d are dissolved with the solvent.

The ion selective electrode and flow type ion sensor using the same according to this invention allow the measurement in a smaller amount of the sample to be measured and are excellent in the adhesion of the ion sensitive membranes, therefore they have effects of a stable potential supply and a prolonged life time, and these industrial merits are highly great.

Further, the ion sensor according to the invention has an advantages that, by using the polyvinyl chloride as the electrode body, the plasticizer in the ion sensitive membrane is diffused to the electrode body side at an adhesive portion so that the adhesion between the ion sensitive membrane and the electrode body of the ion sensor is heightened by the shrinkage of the polyvinyl chloride.

Now, the ion selective electrode and flow type ion sensor using the same according to this invention will be described in detail in reference to an example.

EXAMPLE 1

Each silver layer having an exposed area of 24 mm$^2$ and a thickness of 0.1 mm and connected with a lead wire was mounted on a part of an inner peripheral surface of a through hole having a diameter of 2.5 mm which is provided in the central position of a polyvinyl chloride disc having a diameter of 15 mm and a thickness of 3 mm. Then, this silver layer was employed as an anode and an electrolysis process was carried out to obtain a silver chloride layer on the surface of the silver layer. In this way, there were prepared four polyvinyl chloride discs each in which the silver member was mounted on the through hole inner peripheral surface.

On the other hand, in 20 g of tetrahydrofuran were dissolved 1 g of a polyvinyl chloride resin, 2 g of orthonitrophenyl octyl ether and 130 mg of monensin to prepare a sodium ion sensitive membrane-forming solution; in the same were dissolved 1.1 g of the polyvinyl chloride resin, 1.7 g of dioctyl adipate, 2 mg of potassium tetraphenylborate and 10 mg of valinomycin to prepare a potassium ion sensitive membrane-forming solution; in the same were dissolved 1 g of the polyvinyl chloride resin, 2 g of orthonitrophenyl octyl ether and 20 mg of (−)-(R,R)-N,N-di-[(1-ethoxycarbonyl)undecyl]-N,N-4,5-tetramethyl-3,6-dioxaoctane diamide as a calcium ion selective material to prepare a calcium ion sensitive membrane-forming solution; and in the same were dissolved 1.5 g of the polyvinyl chloride series resin and 500 mg of methyltridodecylammonium chloride to prepare a chloride ion sensitive membrane-forming solution.

Afterward, the obtained sodium, potassium, calcium and chloride ion sensitive membrane-forming solutions were separately applied to the inner peripheral surfaces of the through holes which were provided in the four polyvinyl chloride discs, followed by drying to form ion sensitive membranes of 300 μm in thickness thereon, whereby ion selective electrodes regarding the present invention were obtained.

These ion selective electrodes were mutually integrally associated with each other with the interposition of silicone rubber disc insulating members each having a diameter of 15 mm and a thickness of 3 mm and provided at the center thereof with a through holes of 2.5 mm in diameter so that the respective through holes thereof might define a flow passage for the liquid to be measured, as shown in FIG. 3, whereby the ion sensor according to this invention was obtained.

COMPARATIVE EXAMPLE

On the other hand, for comparison, the same procedure as in Example 1 was repeated with the exception that an acrylic resin disc was employed instead of the polyvinyl chloride disc in Example 1, in order to prepare an ion sensor for comparison.

EXAMPLE 2

Next, a solution including ions of sodium, potassium, calcium and chloride in each concentration of 50 mmol/l was allowed to continuously pass through the flow passage for the liquid to be measured in each case of the ion sensor according to this invention and the ion sensor for comparison which were prepared in Example 1 and Comparative example, for the purpose of carrying out a life time test.

As a result, the ion sensor according to this invention could indicate normal measured values even after 230 days' continuous measurement, but in the case of the ion sensor for comparison, the ion sensitive membranes peeled off within 11 days, and afterward the measurement of ion concentrations was unfeasible.

We claim:
1. A flow type ion sensor which comprises
(i) a first plurality of ion selective electrodes, each ion selective electrode of said first plurality comprising
  (a) a plate comprised of a polyvinyl chloride series resin, said plate having a through hole;
  (b) a conductive member disposed in said plate, said conductive member presenting a surface which faces said through hole;
  (c) an ion sensitive membrane which is comprised of a polyvinyl chloride series resin and which is immediately adjacent to an inner surface of said through hole; and
  (d) a lead wire connected to said conductive member,
  wherein said ion sensitive membrane covers said conductive member and contacts said plate along at least a portion of said inner surface of said through hole, and
(ii) a second plurality of electrical insulating members, each electrical insulating member of said second plurality being interposed between ion selective electrodes of said first plurality such that the respective through holes of said ion selective electrodes define a flow passage.

2. The flow type sensor according to claim 1, wherein said ion sensitive membrane contains an ion selective substance selected from the group consisting of monensin, valinomycin, a quaternary ammonium salt and a crown ether.

3. The flow type ion sensor according to claim 1, further comprising a reference electrode.

4. The flow type ion sensor according to claim 3, wherein said reference electrode comprises:
   (a) a plate comprised of a polyvinyl chloride series resin, said plate having a through hole;
   (b) a conductive member disposed in said plate, said conductive member presenting a surface which faces said through hole;
   (c) an ion sensitive membrane which is comprised of a polyvinyl chloride series resin and which presents a surface facing said through hole;
   (d) a membrane comprised of a silicone series polymer which covers said ion sensitive membrane and which is immediately adjacent to said through hole; and
   (e) a lead wire connected to said conductive member,
   wherein said ion sensitive membrane covers said conductive member and contacts said plate along at least a portion of said inner surface of said through hole.

5. The flow type ion sensor according to claim 4, wherein said reference electrode is a silver-silver halide electrode which comprises (i) a conductive member comprising a substrate comprised of silver and a metallic layer comprised of a silver halide provided on at least a portion of said substrate, said metallic layer facing said flow passage; (ii) an ion sensitive membrane comprised of a polyvinyl chloride series resin which contains potassium chloride, said ion sensitive membrane facing said flow passage and covering said conductive member of said reference electrode; and (iii) a membrane comprised of a silicone series polymer which covers said ion sensitive membrane and which is immediately adjacent to said flow passage.

6. The flow type ion sensor according to claim 3, wherein said reference electrode is a silver-silver halide electrode forming at least a part of said inner surface of said through hole.

7. The flow type ion sensor according to claim 1, wherein said conductive member comprises a metal substrate and a metallic layer provided on said substrate which is comprised of a compound of said metal, said metallic layer facing said inner surface of said through hole.

8. The flow type ion sensor according to claim 7, wherein said substrate comprises silver and said metallic layer comprises a silver halide.

9. The flow type ion sensor according to claim 1, wherein said flow type ion sensor is surrounded with an outer case having an inlet and an outlet for a liquid to be measured, said inlet and said outlet communicate, respectively, with said through holes, and having an electrical signal output opening for leading out the lead wires of said ion selective electrodes.

10. An ion selective electrode which comprises
   (a) a plate comprised of a polyvinyl chloride series resin, said plate having a through hole;
   (b) a conductive member disposed in said plate, said conductive member presenting a surface which faces said through hole;
   (c) an ion sensitive membrane which is comprised of a polyvinyl chloride series resin and which is immediately adjacent to an inner surface of said through hole; and
   (d) a lead wire conneted to said conductive member, wherein said ion sensitive membrane covers said conductive member and contacts said plate along at least a portion of said inner surface of said through hole.

11. The ion selective electrode according to claim 10, wherein said ion selective substance selected from the group consisting of monensin, valinomycin, a quaternary ammonium salt and a crown ether.

12. The ion selective electrode according to claim 10, wherein said conductive member comprises a metal substrate and metallic layer provided on said substrate which is comprised of a compound comprising said metal substrate, said metallic layer facing said inner surface of said through hole.

13. The ion selective electrode according to claim 12, wherein said substrate comprises silver and said metallic layer comprises a silver halide.

* * * * *